United States Patent
Wang et al.

(10) Patent No.: US 8,864,994 B2
(45) Date of Patent: Oct. 21, 2014

(54) METHOD FOR POST-EXTRACTING HIGH-ACYL GELLAN GUM

(75) Inventors: Xuegang Wang, Zhejiang (CN); Rongming Wu, Zhejiang (CN); Zhiming Zhang, Zhejiang (CN); Jialiang Wang, Zhejiang (CN); Huaiyuan Xu, Jiangxi (CN); Yubin Shen, Zhejiang (CN); Liqiang Yang, Zhejiang (CN)

(73) Assignee: Zhejiang DSM Zhongken Biotechnology Co., Ltd., Zhejiang (CN)

( * ) Notice: Subject to any disclaimer, the term of this patent is extended or adjusted under 35 U.S.C. 154(b) by 680 days.

(21) Appl. No.: 13/142,379

(22) PCT Filed: Jun. 2, 2010

(86) PCT No.: PCT/CN2010/000784
§ 371 (c)(1), (2), (4) Date: Jun. 27, 2011

(87) PCT Pub. No.: WO2010/139191
PCT Pub. Date: Dec. 9, 2010

(65) Prior Publication Data
US 2011/0269189 A1    Nov. 3, 2011

(30) Foreign Application Priority Data
Jun. 3, 2009   (CN) .......................... 2009 1 0143908

(51) Int. Cl.
*C02F 3/00* (2006.01)
*C12P 19/04* (2006.01)
*C08B 37/00* (2006.01)

(52) U.S. Cl.
CPC ............... *C12P 19/04* (2013.01); *C08B 37/006* (2013.01); *C08B 37/0003* (2013.01)
USPC ........................... 210/606; 210/723; 210/724

(58) Field of Classification Search
USPC ........................................ 210/606, 723–724
See application file for complete search history.

(56) References Cited

U.S. PATENT DOCUMENTS

| 5,284,587 A * | 2/1994 | Wong et al. .................. 210/606 |
| 6,605,461 B2 | 8/2003 | Yamazaki et al. |
| 2008/0145505 A1 | 6/2008 | Bezanson et al. |

FOREIGN PATENT DOCUMENTS

| CN | 101062957 A | 10/2007 |
| CN | 101585886 A | 11/2009 |

* cited by examiner

*Primary Examiner* — Chester Barry
(74) *Attorney, Agent, or Firm* — Drinker Biddle & Reath LLP

(57) ABSTRACT

Disclosed is a method for extracting high acyl gellan from the fermentation broth containing gellan gum with a low production cost and high quality of products, comprising the following steps: (1) Treatment of the fermentation broth with an enzyme; (2) flocculation of the treated fermentation broth with acid; (3) wash of the fiber-like material; and (4) drying and milling.

23 Claims, No Drawings

METHOD FOR POST-EXTRACTING HIGH-ACYL GELLAN GUM

TECHNICAL FIELD OF INVENTION

This invention relates to the field of fermentation of a microorganism, particularly, relates to a post extraction process for preparing high acyl gellan.

BACKGROUND

Gellan gum is a hydrophilic colloid produced by the fermentation of a bacterium, *Sphingomonas paucimobilis*, which is a strain screened and separated from the nature by a broad selection. Gellan gum has a lot of useful properties.

The basic structure of the molecule of gellan gum is a main chain, constituted by the repeating units of four sugars. The single sugars participating the formation of the repeating units include glucose, rhamnose and glucuronic acid. In the original form of gellan gum, i.e., high acyl gellan, two substituents, including acetyl groups and glyceryl groups, co-exist. The two kinds of groups are located on the same glucose residue. For each repeat unit, there is a glyceryl group; and for every two repeat units, there is an acetyl group. In the low acyl gellan gum, the acyl groups are removed completely. The acyl groups have a significant influence on the property of gel. High acyl-type gellan gum produces a gel having the property of softness, full of flexibility and not having brittleness, while the low acyl-type gellan gum produces a gel having the property of firmness, not having flexibility, but with brittleness. As to the marketed gellan products, gellan gum has two kinds: one is the low acyl gellan gum, i.e., the acyl groups in the main chain of the molecule of gellan gum were removed completely or partially; and the other is the natural gellan gum, i.e., high acyl gellan.

High acyl gellan can play a good role in gelation, shaping, fixation and film-forming. And high acyl gellan has the following characteristics: being a shear force reversible and thermo reversible gel, having an excellent emanation property of fragrances, being able to be used with other aqueous gels, having cooperatively with starch, having an extremely good shaping role, being an elastic gel, and being able to improve the flavors. Therefore, high acyl gellan has broad applications in pharmaceutical, chemical and food industries. High acyl gellan is a good substitute of carrageenan, agar, pectin and other hydrophilic colloids, and has a high demand in markets.

At present, the oversea production of high acyl gellan is only conducted by CP Kelco Inc., a USA entity, whose production method has not been reported in our country. In our country, the extraction method for high acyl gellan comprises the following steps: firstly sterilizing the bacterium by high temperature and then flocculently depositing by adding an alkali metal chloride and isopropanol (Zany et al, A method of post extraction of high acyl gellan, China Patent Application Publication No. CN1687437A). The method has the following defects:

1. The method uses calcium chloride, a new impurity, introduced during the flocculation; and
2. The high acyl gellan product obtained by using this method has a poor appearance, a low purity, low gel strength, and a poor solubility.

SUMMARY OF INVENTION

One aim of the present invention is to provide an extraction method for extracting high acyl gellan from the fermentation broth containing gellan gum, with a low cost in production and providing a product having a good quality.

The general technical concept of the present invention includes:

The method for extracting high acyl gellan according to the present invention includes: a treatment of a fermentation broth containing gellan gum with enzyme, a flocculation with acid, a first solid-liquid separation, a wash of the solid fiber-like material, a second solid-liquid separation, and a drying and crushing of the solid material. In particular, the specific steps are:

(1) Treatment of Fermentation Broth with Enzyme.

Adding an enzyme preparation into the fermentation broth to react by raising the temperature;

(2) Flocculation of Fermentation Broth with Acid.

Cooling down the fermentation broth treated by the enzyme in step (1), and flocculating it by adding an acid into it, then separating the solid from the liquid;

(3) Wash of the Fiber-Like Material.

Washing the solid fiber-like material obtained after the solid-liquid separation in step (2) firstly with a low polar or non-polar solvent, and separating the solid from the liquid, and then, again washing the solid fiber-like material with a lower alcohol and again separating the solid from the liquid; and (4) Drying and Crushing.

Drying the solid material obtained in step (3) and crushing the dried solid material, thereby the high acyl gellan product is obtained.

More particularly, the method comprises the following steps:

(1) Treatment of Fermentation Broth with Enzyme

Adding 100 ppm enzyme preparation into the fermentation broth on basis of the volume of the fermentation broth, which has been dispersed and dissolved in a little amount of water, and then raising the temperature of the fermentation broth to 50-60° C., and keep at the temperature for 4~6 hrs;

(2) Flocculation of Fermentation Broth with Acid

Cooling down the material in step (1) to a temperature below 35° C., and adjust the pH to pH 1.5~4 by adding an acid to form a fiber-like flocculent, and then conducting a solid-liquid separation;

(3) Wash of the Fiber-Like Material (3.1) wash with a low polar or non-polar solvent. Adding one time or two times low polar or non-polar solvent into the material prepared in step (2), and adjusting the pH to pH 4.5~8 with a base, and washing for 2 hrs, and conducting a solid-liquid separation; (3.2) wash with lower alcohol. Adding 4~5 times of lower alcohol into the material prepared in step (3.1), and washing for 2 hrs, and conducting a solid-liquid separation.

(4) Drying and Crushing

Vacuum drying the product prepared in step (3) at the temperature of 75~80° C., and crushing the dried product and thereby obtaining the high acyl gellan product.

The specific processing conditions for each step of the present invention are:

The enzyme used in step (1) is a single enzyme or a combination of enzymes, selected from the group consisting of a neutral protease, an alkaline protease, an acidic protease, papain, and lysozyme. And all the enzymes used are high temperature-tolerant enzymes. If the enzyme is a combination or mixture of enzymes, the enzymes in the mixture can be mixed at any ratio. Preferably, a combination of alkaline protease and lysozyme is used with the weight ratio of 5:1.

The concentration of the acid used in step 1 is 10%.

The acid used in step 2 is selected from the group consisting of acetic acid, citric acid, hydrochloric acid, and sulfuric acid. Preferably, acetic acid is used.

The solid-liquid separation in step 2 is conducted with a chamber-type polypropylene plate-and-frame filter press.

The low polar or non-polar solvent in step 3.1 is acetone, butanone, ethyl ether, or n-hexane. Preferably, the solvent is acetone.

The concentration of the base used in step 3.1 for adjusting pH is 10%.

The base used in step 3.1 for adjusting pH is selected from the group consisting of NaOH, KOH, $Na_2CO_3$, and $K_2CO_3$.

The lower alcohol used in step 3.2 is selected from the group consisting of methanol, ethanol, and isopropanol.

The solid-liquid separation device used in step 3 is a pressafiner.

The temperature for vacuum drying in step 4 is a temperature in the range of 75~80° C.

The vacuum degree of the vacuum drying in step 4 is −0.09 mp.

The time for the vacuum drying in step 4 is 1.5 hrs.

EMBODIMENTS

The following examples are provided to illustrate the present invention with more details. The examples are provided for a better understanding of the invention, do not to limit the present invention. The examples are non-limited.

Example 1

A. Taking an amount of fermentation broth containing gellan gum that were formed by a fermentation, and adding 100 ppm alkaline protease and lysozyme into the fermentation broth under agitation. The temperature of the mixture formed was raised up to 55° C. and maintained for 5 hrs under agitation. Then, the temperature of the mixture was dropped down to 32° C.;

B. Into the above mixture, 10% of acetic acid solution was added gently and slowly until the pH of the mixture reached 2.0. The addition of acetic acid solution was stopped and the mixture was kept at this condition for 10 minutes. Then, the mixture was pumped into a chamber-type plate-and-frame filter press with a pump to filter. The filtrate was exited to the disposal station for waste water, and the filter cake was kept for later-use;

C. Into the filter cake obtained in Step B, 2 times of acetone calculated by weight was added and the pH was adjusted to pH 6.0 with 10% of NaOH solution. The mixture was washed for 2 hrs, and then the mixture was pumped into a pressafiner for a solid-liquid separation. The liquid was recovered with rectification tower to recover the acetone, and the solid was taken subjected to the next step;

D. Into the material obtained in Step C, 4 times of ethanol was added. The mixture was washed for 2 hrs and then pumped into a pressafiner for a solid-liquid separation. The liquid was entered into a rectification tower to recover ethanol, and the solid was taken subjected to the next step.

E. Drying the fiber-like solid obtained from step D by vacuum drying, with the drying temperature of 78° C., the degree of vacuum of −0.09 mp, and the drying time of 1.5 hrs. And then, the dried material was milled by a miller and produced a nearly white powder, i.e., high acyl gellan product.

Example 2

A. Taking the fermentation broth containing gellan gum produced after the termination of fermentation, and adding 100 PPM of papain into to it under agitation. Then the temperature was raised up to 55° C., and the agitation was kept for 5 hrs, and the temperature was dropped down to 30° C.;

B. Into the above solution, 10% of hydrochloric acid solution was slowly added until the pH of the solution reached pH 2.5. Stopping the addition, and keeping the mixture under the agitation for 10 min. The solution was pumped into the chamber-type plate-and-frame filter press to filter. The filtrate was exited into the waste water station, and the filter cake was stored for later use;

C. The filter cake obtained in step B was 5 times of ethyl ether in the basis of weight, and the pH of the mixture was adjusted to 5.3 with 10% KOH solution. Then, the mixture was agitated and washed for 2 hrs, and then was pumped into a pressafiner for a solid-liquid separation. The liquid phase was forced into rectification tower for the recovery of ethyl ether, and the solid phase was subjected to the next step treatment;

D. The material obtained in step C was added into 4.5 times of ethanol in the basis of weight, and agitated and washed for 2 hrs. Then, the mixture was pumped into a pressafiner for a solid-liquid separation. The liquid phase was forced into rectification tower for the recovery of ethanol, and the solid phase was subjected to the treatment of the next step; and E. The fiber-like solid obtained in step D was subjected to a vacuum drying. The temperature for the vacuum drying is 80° C., with the degree of vacuum being −0.09 mp, and the time for drying being 1.5 hours. After the drying, and later conducting a milling by a miller, a whitish power was obtained, which is the high acyl gellan product.

In view of the existing post extraction processes for preparing high acyl gellan, the process according to the present invention has the following advantages, among others:

1. The whole process according to the present invention has a low energy consumption compared with the existing processes because there is no need to sterilize the fermentation broth with high temperature.

2. The amount of raw materials was decreased. The invention only used an organic acid during the deposition by flocculation, without the introduction of new calcium ions or other alkali metals ions as impurities.

3. The quality of product was improved greatly, reaching the advanced level oversea. The appearance of the product was good, with a high purity. The gel strength of the product is high and the solubility of the product was improved largely. For details, see the following table:

| Post Extraction Processes for Preparing High Acyl Gellan in the existing prior art technologies | The process according to the present invention |
|---|---|
| chroma ≥60% | chroma ≥75% |
| purity ≥70% | purity ≥80% |
| gel strength (0.5% concentration) 300~400g/cm$^2$ | gel strength (0.5% concentration) 450~600g/cm$^2$ |
| solubility It can dissolve in a water bath of 80° C. within 5~6 minutes | solubility It can dissolve in a water bath of 80° C. within 1~2 minutes |

What is claimed is:

1. A post extraction process for preparing high acyl gellan, comprising the following steps:
   (1) Adding an enzyme preparation into a fermentation broth to conduct a reaction by raising the temperature of the broth;

(2) Cooling down the fermentation broth treated by the enzyme in step (1), adding an acid to flocculate the fermentation broth, and then conducting a solid-liquid separation;

(3) Washing the solid fiber-like material obtained from the solid-liquid separation in step (2) first with a low polar or non-polar solvent, then conducting a solid-liquid separation, and then washing the solid fiber-like material with a lower alcohol, and then conducting a solid-liquid separation; and (4) Drying and disintegrating the solid material obtained in step (3), to obtain the high acyl gellan product.

2. The post extraction process for preparing high acyl gellan according to claim 1, characterized in that the enzyme used in step (1) is one enzyme or a combination of more than one enzyme, wherein the enzymes are selected from the group consisting of neutral protease, alkaline protease, acidic protease, papain, and lysozyme.

3. The post extraction process for preparing high acyl gellan according to claim 1, characterized in that the enzyme used in step (1) is a combination of an alkaline protease and a lysozyme, with the two enzymes of alkaline protease and lysozyme in the combination in the weight ratio of 5:1.

4. The post extraction process for preparing high acyl gellan according to claim 1, characterized in that the amount of the enzyme preparation is used at the final concentration of 100 ppm, on the basis of the volume of the fermentation broth.

5. The post extraction process for preparing high acyl gellan according to claim 1, characterized in that the enzyme is firstly dissolved and dispersed with a small amount of water, and then added.

6. The post extraction process for preparing high acyl gellan according to claim 1, characterized in that the reaction by raising the temperature in step (1) is conducted by raising the temperature up to 50-60° C. and maintaining the temperature for 4-6 hours.

7. The post extraction process for preparing high acyl gellan according to claim 1, the flocculation with an acid in step (2) is to cool down the material of step (1) to a temperature below 35° C., to add the acid into the material to adjust the pH to a pH in the range of 1.5-4, and form the fiber-like flocculates, and then to conduct said solid-liquid separation.

8. The post extraction process for preparing high acyl gellan according to claim 1, characterized in that the acid used in step 2 is at the concentration of 10%.

9. The post extraction process for preparing high acyl gellan according to claim 1, characterized in that the acid used in step 2 is one selected from the group consisting of acetic acid, citric acid, hydrochloric acid, and sulfuric acid.

10. The post extraction process for preparing high acyl gellan according to claim 1, characterized in that the acid used in step 2 is acetic acid.

11. The post extraction process for preparing high acyl gellan according to claim 1, characterized in that the device used for the solid-liquid separation in step 2 is a chamber-type plate-and-frame filter press.

12. The post extraction process for preparing high acyl gellan according to claim 1, characterized in that the wash with a nonpolar solvent in step (3) is: taking the material prepared in step (1), adding the non-polar solvent in the amount of 1 to 2 times of the material in weight into the material, and adjusting to pH 4.5-8 with a base and washing 2 hours and conducting the solvent washing step solid-liquid separation step.

13. The post extraction process for preparing high acyl gellan according to claim 12, characterized in that the low polar or non-polar solvent used in step 3 is one selected from the group consisting of acetone, butanone, ethyl ether, and n-hexane.

14. The post extraction process for preparing high acyl gellan according to claim 12, characterized in that the low polar or non-polar solvent in step 3 is acetone.

15. The post extraction process for preparing high acyl gellan according to claim 12, characterized in that the base in step 3 is used at the concentration of 10%.

16. The post extraction process for preparing high acyl gellan according to claim 12, characterized in that the base used in step 3 is one selected from the group consisting of NaOH, KOH, $Na_2CO_3$, and $K_2CO_3$.

17. The post extraction process for preparing high acyl gellan according to claim 1, characterized in that the wash with alcohol in step (3) is to add the lower alcohol in the amount of 4-5 times of the material in weight into the material and wash 2 hours, and conduct the alcohol washing step solid-liquid separation step.

18. The post extraction process for preparing high acyl gellan according to claim 17, characterized in that the lower alcohol used in step (3) is at the concentration of 90-95%.

19. The post extraction process for preparing high acyl gellan according to claim 17, characterized in that the lower alcohol as used is one selected from the group consisting of methanol, ethanol, and isopropanol.

20. The post extraction process for preparing high acyl gellan according to claim 1, characterized in that the device used in each of the solid-liquid separation steps in step (3) is a screw press.

21. The post extraction process for preparing high acyl gellan according to claim 1, characterized in that the drying in step 4 is a vacuum drying and the temperature for the vacuum drying is 75-80° C.

22. The post extraction process for preparing high acyl gellan according to claim 1, characterized in that the drying in step 4 is a vacuum drying and the degree of the vacuum drying is −0.09 mPa.

23. The post extraction process for preparing high acyl gellan according to claim 1, characterized in that the drying in step 4 is a vacuum drying, and the time for the vacuum drying is 1.5 hours.

* * * * *